(12) United States Patent
Hruby et al.

(10) Patent No.: US 11,542,302 B2
(45) Date of Patent: Jan. 3, 2023

(54) MODULATORS OF MELANOCORTIN RECEPTORS FOR THE TREATMENT OF DEPRESSION AND ANXIETY

(71) Applicants: ARIZONA BOARD OF REGENTS ON BEHALF OF THE UNIVERSITY OF ARIZONA, Tucson, AZ (US); THE TEXAS A&M UNIVERSITY SYSTEM, College Station, TX (US)

(72) Inventors: Victor J. Hruby, Tucson, AZ (US); Minying Cai, Tucson, AZ (US); Caurnel Morgan, College Station, TX (US)

(73) Assignees: ARIZONA BOARD OF REGENTS ON BEHALF OF THE UNIVERSITY OF ARIZONA, Tucson, AZ (US); THE TEXAS A&M UNIVERSITY SYSTEM, College Station, TX (US)

( * ) Notice: Subject to any disclaimer, the term of this patent is extended or adjusted under 35 U.S.C. 154(b) by 172 days.

(21) Appl. No.: 16/876,683

(22) Filed: May 18, 2020

(65) Prior Publication Data
US 2020/0277331 A1    Sep. 3, 2020

Related U.S. Application Data

(63) Continuation-in-part of application No. 16/342,371, filed as application No. PCT/US2016/057353 on Oct. 17, 2016, now abandoned, application No. 16/876,683, which is a continuation-in-part of application No. 15/768,267, filed as application No. PCT/US2016/057329 on Oct. 17, 2016, now Pat. No. 10,653,743.

(60) Provisional application No. 62/242,228, filed on Oct. 15, 2015.

(51) Int. Cl.
| | | |
|---|---|---|
| A61K 38/12 | (2006.01) | |
| A61K 38/34 | (2006.01) | |
| C07K 14/68 | (2006.01) | |
| A61K 38/00 | (2006.01) | |
| A61P 25/18 | (2006.01) | |
| A61P 25/22 | (2006.01) | |
| A61P 25/24 | (2006.01) | |
| A61K 38/08 | (2019.01) | |
| A61K 38/06 | (2006.01) | |
| A61K 38/07 | (2006.01) | |
| C07K 5/02 | (2006.01) | |
| A61K 9/00 | (2006.01) | |
| A61K 9/70 | (2006.01) | |

(52) U.S. Cl.
CPC .......... *C07K 5/0202* (2013.01); *A61K 9/0019* (2013.01); *A61K 9/0053* (2013.01); *A61K 9/7023* (2013.01); *A61K 38/07* (2013.01);

*A61K 38/12* (2013.01); *A61P 25/22* (2018.01); *A61P 25/24* (2018.01); *A61K 38/00* (2013.01)

(58) Field of Classification Search
None
See application file for complete search history.

(56) References Cited

U.S. PATENT DOCUMENTS

| | | |
|---|---|---|
| 6,054,556 A | 4/2000 | Hruby et al. |
| 7,754,691 B1 | 7/2010 | Sharma |
| 7,795,378 B2 | 9/2010 | Sharma et al. |
| 9,458,195 B2 | 10/2016 | Dong et al. |
| 9,814,755 B2 | 11/2017 | Hruby et al. |
| 9,821,023 B2 | 11/2017 | Hruby et al. |
| 9,850,280 B2 | 12/2017 | Dong et al. |
| 2002/0143141 A1 | 10/2002 | Chen et al. |

(Continued)

FOREIGN PATENT DOCUMENTS

| | | |
|---|---|---|
| WO | WO2005079574 A1 | 9/2005 |
| WO | WO2014136118 A1 | 9/2014 |

(Continued)

OTHER PUBLICATIONS

Greico et al. "Design and Microwave-Assisted Synthesis of Novel Macrocyclic Peptides Active at Melanocortin Receptors: Discovery of Potent and Selective hMC5R Receptor Antagonists," J. Med. Chem., May 8, 2008 (May 8, 2008), vol. 51, vol. 9, pp. 2701-2707 and Supporting Information.

(Continued)

*Primary Examiner* — Thea D' Ambrosio
(74) *Attorney, Agent, or Firm* — Nguyen Tarbet LLC

(57) ABSTRACT

Compositions and methods for treating a depressive disorder or an anxiety disorder in a subject in need of such treatment are described herein. A therapeutically effective amount of a composition comprising a melanocortin 5 receptor (MC5R) peptide ligand according to the following:

(SEQ ID NO: 1)

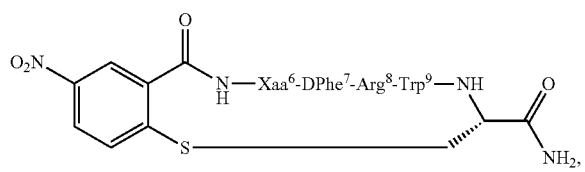

in a pharmaceutically acceptable carrier is administered to the subject. Xaa can be Cha or Pro. The MC5R peptide is a selective MC5R antagonist, and administration thereof to the subject can treat the depressive or anxiety disorder with clinical improvement observed in a relatively short time.

18 Claims, No Drawings
Specification includes a Sequence Listing.

(56) References Cited

U.S. PATENT DOCUMENTS

| | | |
|---|---|---|
| 2005/0124553 A1 | 6/2005 | Sharma et al. |
| 2010/0129319 A1 | 5/2010 | Lindquist et al. |
| 2011/0183886 A1 | 7/2011 | Dong et al. |
| 2015/0037376 A1 | 2/2015 | Seth et al. |
| 2017/0020952 A1 | 1/2017 | Hruby et al. |
| 2017/0020953 A1 | 1/2017 | Hruby et al. |
| 2018/0319843 A1 | 11/2018 | Hruby et al. |

FOREIGN PATENT DOCUMENTS

| | | |
|---|---|---|
| WO | WO2017066754 A1 | 4/2017 |
| WO | WO2018074999 A1 | 4/2018 |

OTHER PUBLICATIONS

Mayorov et al. "Effects of Macrocycle Size and Rigidity on Melanocortin Receptor-I and Selectivity in Cyclic Lactam a-Melanocyte-Stimulating Hormone Analogs," Chem Bioi Drug Des., Jun. 9, 2006 (Jun. 9, 2006), vol. 67, No. 5, pp. 329-335.

Hruby. VJ et al. Approaches to the Rational Design of Selective Melanocortin Receptor Antagonists. Expert Opinion on Drug Discovery. May 2011. vol. 6. Issue 5. pp. 543-557.p. 9. paragraph (4); p. 24. table 5.

Is This the Best New Solution to the Depression Epidemic, available online at https://thebestbrainpossible.com/is-this-the-best-new-solution-to-the-depression-epidemic/, 16 pages(Aug. 2016) (Year: 2016).

International Search Report Issued for PCT Application No. PCT/US16/57329 dated Jan. 10, 2017.

International Search Report Issued for PCT Application No. PCT/US16/57353 dated Mar. 23, 2017.

Grieco et al. "Design and Synthesis of Highly Potent and Selective Melanotropin Analogues of SHU9119 Modified at Position 6" Biochm. Biophy. Res. Comm. 2002; 292:1075-1080.

Liu et al. "The Melanocortinergic Pathway Is Rapidly Recruited by Emotional Stress and Contributes to Stress-Induced Anorexia and Anxiety-Like Behavior" Endocrinology, 2007; 148:6631-5540.

Stankova, dissertation, The Univeristy of Arizona, 2004.

Biology Online, "Treat," available online at https://www.biology-online.org/dictionarylTreat, 1 page (accessed on Feb. 15, 2020) (Year:2020).

Truschel, "Types of Depression: The 10 Most Common Depressive Disorders," available online at https://www.psycom.net/10-types-of-depression/, 18 pages (2019) (Year: 2019).

U.S. Department of Health & Human Services, "What are the five major types of anxiety disorders," available online at https://www.hhs.gov/answers/mental-health-and-substance-abuse/what-are-the-five-major-types-of-anxiety-disorders/index.html, 2 pages (accessed on Feb. 15, 2020) (Year: 2020).

MODULATORS OF MELANOCORTIN RECEPTORS FOR THE TREATMENT OF DEPRESSION AND ANXIETY

CROSS REFERENCE

This application is a continuation-in-part and claims benefit of U.S. patent application Ser. No. 16/342,371 filed Apr. 16, 2019, which is a 371 of PCT/US16/57353 filed on Oct. 17, 2016, the specifications of which are incorporated herein in their entirety by reference.

This application is a continuation-in-part and claims benefit of U.S. patent application Ser. No. 15/768,267 filed Apr. 13, 2018, which is a 371 of PCT/US16/57329 filed on Oct. 17, 2016, which claims priority to U.S. Provisional Application No. 62/242,228, filed Oct. 15, 2015, the specifications of which are incorporated herein in their entirety by reference.

REFERENCE TO SEQUENCE LISTING

Applicant asserts that the written sequence listing is identical to the sequence listing information recorded in computer readable form found on the accompanying computer file entitled UNIA_15_37_PCT2_US_CIP_Sequence_Listing_ST25. The content of the sequence listing is incorporated herein by reference in its entirety.

FIELD OF THE INVENTION

The present invention relates to compositions and methods for treating depression or anxiety, in particular, treating depression or anxiety with melanocortin 5 receptor (MC5R) antagonists.

BACKGROUND OF THE INVENTION

Depression and anxiety are some of the most common mental illnesses. Although the two are different, depression and anxiety can occur together and can have similar treatments. These disorders can be treated through psychotherapy and medications, such as anti-depressants. Unfortunately, current medications may take weeks to months to achieve their full effects and in the meantime, patients continue to suffer from their symptoms and continue to be at risk. Moreover, side effects from these medications can range from unpleasant to life-threatening; for instance, there can be an increased risk of suicide, hostility, and even homicidal behavior. Hence, there remains a need for pharmacological treatments that have a rapid onset of antidepressant or anti-anxiety effects within hours or a few days and that are sustained while reducing or eliminating any potential side effects.

Melanocortin receptors, MC1-5R are a family of five receptor compounds of the melanocortin receptor system. Prior to the invention, it has been difficult to target the receptors independently of one another. The present invention is specific to individual types of melanocortin receptors, specifically to MC5R, and can therefore modulate the MC5R for treating depression and anxiety.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

In one embodiment, the present invention features a composition for use in treating a depressive disorder or an anxiety disorder. The composition for use comprises a melanocortin 5 receptor (MC5R) peptide ligand according to the following:

(SEQ ID NO: 1)

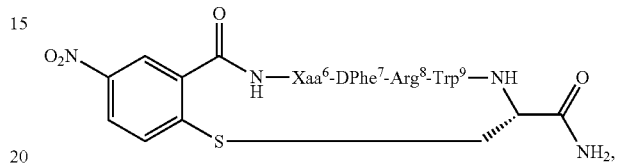

in a pharmaceutically acceptable carrier. In some aspects, Xaa is cyclohexylalanine (Cha) or Pro.

In another embodiment, the subject disclosure features method of treating a depressive disorder or an anxiety disorder in a subject in need of such treatment. The method may comprise administering to the subject a therapeutically effective amount of a composition comprising a melanocortin 5 receptor (MC5R) peptide ligand according to the following:

(SEQ ID NO: 1)

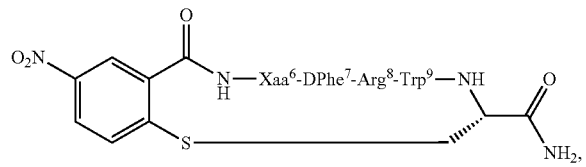

in a pharmaceutically acceptable carrier. In some aspects, Xaa is cyclohexylalanine (Cha) or Pro.

One of the unique and inventive technical features of the present invention is the MC5R peptide ligand for use in treating the depressive disorder or anxiety disorder. Without wishing to limit the invention to any theory or mechanism, it is believed that the technical feature advantageously provides for a potent MC5R antagonist that can treat the disorder in a relatively short period of time as compared to conventional treatments. None of the presently known prior references or work has the unique inventive technical feature of the present invention.

DESCRIPTION OF PREFERRED EMBODIMENTS

Before the present compounds, compositions, and/or methods are disclosed and described, it is to be understood that this invention is not limited to specific synthetic methods or to specific compositions, as such may, of course, vary. It is also to be understood that the terminology used herein is for the purpose of describing particular embodiments only and is not intended to be limiting.

The melanocortin 5 receptor (MC5R) peptide ligands of the present invention is based on Melanotan II (MT-II), Ac-Nle$^4$-c[(Asp$^5$-His$^6$-DPhe$^7$-Arg$^8$-Trp$^9$-Lys$^{10}$]-NH$_2$,
where in the core sequence "His$^6$-DPhe$^7$-Arg$^8$-Trp", His is replaced with Cha or Pro.

As used herein, "clinical improvement" may refer to a noticeable reduction in the symptoms of a disorder, or cessation thereof.

As defined herein, the term "antagonist" refers to compound that diminishes a response. The antagonist binds to the same site as the endogenous compound and diminishes or blocks the signal generated by the endogenous agent.

The term "antidepressant effect" is used in the conventional sense. It is associated with a reversal of or a reduction in the severity of a depressed mood or state of mind.

The term "anxiolytic effect" is used in the conventional sense. It is associated with an inhibition, a reversal of, a reduction in the severity of symptoms of anxiety.

The term "psychostimulating effect", as the term implies, is associated in an increase or improvement in the overall level of mental activity. It is related to patients exhibiting nervous behavior, or having unpleasant feelings of dread, or lacking energy, drive and desire, or lacking concentration and memory. Common psychostimulating effects may include, but are not limited to, enhanced alertness, awareness, wakefulness, endurance, productivity, motivation, increased arousal, and locomotion (i.e. movement or increased energy). The psychostimulants, such as those comprising the MC5R peptide ligands described herein, may also be capable of improving mood and relieving anxiety, and can even induce feelings of euphoria.

According to one embodiment, the present invention may feature a method of treating a depressive disorder or an anxiety disorder in a subject in need of such treatment. According to one embodiment, the method may comprise administering to the subject a therapeutically effective amount of a composition comprising a melanocortin 5 receptor (MC5R) peptide ligand. The MC5R peptide ligand may comprise the following:

(SEQ ID NO: 1)

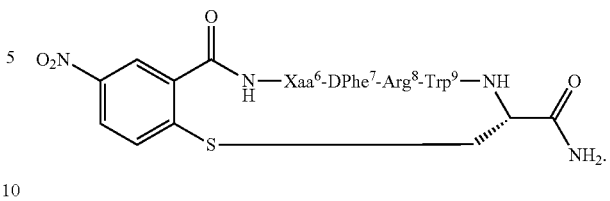

In preferred embodiments, Xaa is cyclohexylalanine (Cha) or Pro.

In some embodiments, the subject may be a mammal, such as a human. In other embodiments, the composition is administered in a dosage of about 0.001 mg/kg to 100 mg/kg of body weight. For example, the dosage may range from about 0.001 to 1 mg/kg, with a preferred range of about 0.01 to 0.1 mg/kg.

In one embodiment, the composition may be administered once daily or twice daily. In another embodiment, the composition may be administered at least once daily, at least once every other day, or at least once weekly. In other embodiments, the composition may be administered intravenously, transdermally, or orally. In preferred embodiments, the composition for use in the treatment resulted in clinical improvement of the depressive disorder or anxiety disorder that is observed in about 1 to 14 days. For example, clinical improvement may be observed in about 1 to 7 days or about 7 to 14 days. Along with clinical improvement, the composition may be effective to evoke at least one of a psychostimulating effect, an anxiolytic effect, or an antidepressant effect.

According to another embodiment, the present invention features a composition for use in treating a depressive disorder or an anxiety disorder. The composition for use comprises a melanocortin 5 receptor (MC5R) peptide ligand. The MC5R peptide ligand may comprise the following:

(SEQ ID NO: 1)

(SEQ ID NO: 1)

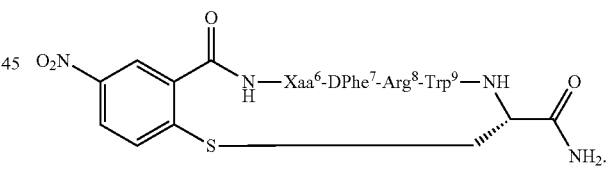

In preferred embodiments, Xaa is cyclohexylalanine (Cha) or Pro. The composition may be capable of treating the depressive disorder or the anxiety disorder such that clinical improvement is observed in about 1 to 14 days. For example, clinical improvement may be observed in about 1-7 days or about 7-14 days. Moreover, administration of the composition may be effective to evoke at least one of a psychostimulating effect, an anxiolytic effect, or an antidepressant effect.

In another embodiment, the method of treating a depressive disorder or an anxiety disorder may comprise determining if the subject has the depressive disorder or the anxiety disorder, and administering a therapeutically effective amount of the composition to the subject if it is determined that the subject has the depressive disorder or the anxiety disorder. The composition may comprise the MC5R peptide ligand according to SEQ ID NO: 1:

In some embodiments, Xaa is cyclohexylalanine (Cha) or Pro. In some embodiments, the composition may be administered to a subject who has been diagnosed with the depressive disorder or the anxiety disorder.

In some embodiments, the composition for use may be administered once daily or twice daily. In another embodiment, the composition may be administered at least once daily, at least once every other day, or at least once weekly. In other embodiments, the composition is administered at a daily dose ranging from about 0.001 mg/kg to 100 mg/kg of body weight. Further still, the composition may be administered intravenously, transdermally, or orally. In preferred embodiments, the composition for use in the treatment resulted in clinical improvement of the depressive disorder or anxiety disorder that is observed in about 1 to 14 days. For example, clinical improvement may be observed in about 1 to 7 days or about 7 to 14 days. Preferably, the composition may be effective to evoke at least one of a psychostimulating effect, an anxiolytic effect, or an antidepressant effect.

In any of the aforementioned embodiments, the composition may be administered in a dosage of about 0.001 mg/kg to 100 mg/kg of body weight. For example, the dosage may range from about 0.001 mg/kg to 0.01 mg/kg of body weight, 0.01 mg/kg to 0.1 mg/kg of body weight, or 0.1 mg/kg to 1 mg/kg of body weight, or about 1 mg/kg to 10 mg/kg of body weight, or about 10 mg/kg to 20 mg/kg of body weight, or about 20 mg/kg to 30 mg/kg of body weight, or about 30 mg/kg to 40 mg/kg of body weight, or about 50 mg/kg to 60 mg/kg of body weight, or about 60 mg/kg to 70 mg/kg of body weight, or about 70 mg/kg to 80 mg/kg of body weight, or about 80 mg/kg to 90 mg/kg of body weight, or about 90 mg/kg to 100 mg/kg of body weight.

Examples of depressive disorders may include, but are not limited to, major depressive disorders or persistent depressive disorders. Examples of anxiety disorders may include, but are not limited to, generalized anxiety disorders or panic disorders.

Without wishing to limit the invention to a particular theory or mechanism, the MC5R peptide ligand is a selective MC5R antagonist that can block MC5R, and is therefore potentially therapeutic for treating depression and anxiety.

TABLE 1 shows non-limiting examples of biological activities of the peptide ligands of the present invention.

often by decreased interest or pleasure in activities. As used herein, a major depressive disorder (MDD) is a common disorder of mood and affect characterized by one or more major depressive episodes. These episodes are defined diagnostically using a criteria-based syndrome listed and described in literature as would be known to one of ordinary skill in the art. These episodes are diagnosed in a human patient if the patient has experienced 5 symptoms from a list of 9 symptom categories every day, or nearly every day, for a period lasting at least 2 weeks. At least one symptom must be present from either category 1 (having a sad, depressed, empty, or irritable mood, or appearing sad to others), or category 2 (experiencing loss of interest in or pleasure from activities). The other symptom categories include: 3) change in weight and/or appetite, 4) insomnia or hypersomnia, 5) psychomotor agitation or retardation, 6) fatigue and/or loss of energy, 7) feelings of worthlessness and/or excessive or inappropriate guilt, 8) diminished ability to think or of concentrate and/or indecisiveness, and 9) recurrent thoughts of death or suicide.

Persistent depressive disorder, also known as dysthymia, is a chronic (ongoing) type of depression in which a person's moods are regularly low. However, the symptoms are not as severe as with major depression.

Bipolar Disorder (also known as "manic-depressive illness") is a mood disorder arising in a human patient who

| SEQ ID NO: | MC5R Peptide Ligand | hMC5R | | |
|---|---|---|---|---|
| | | *$IC_{50}$ (nM) | †$EC_{50}$ (nM) | ‡% Act at 10 μM |
| 2 | 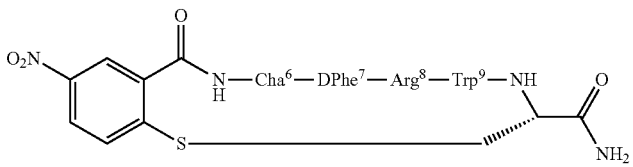 | 38 ± 3 | na | 0 |
| 3 | 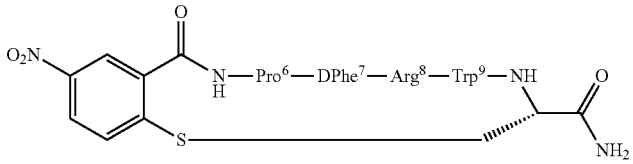 | 58 ± 6 | na | 0 |

*$IC_{50}$ = concentration of peptide at 50% specific binding (N = 4).
†$EC_{50}$ = Effective concentration of peptide that was able to generate 50% maximal intracellular cAMP accumulation (N = 4).
‡% max effect = % of cAMP produced at 10 μM ligand concentration, in relation to MT-II. The peptides were tested in a range of concentrations from $10^{-10}$ to $10^{-5}$ μM.
na: no activity at $10^{-5}$ M.

Disclosed are the various compounds, solvents, solutions, carriers, and/or components to be used to prepare the disclosed compositions as well as the compositions themselves to be used within the methods disclosed herein. Also disclosed are the various steps, elements, amounts, routes of administration, symptoms, and/or treatments that are used or observed when performing the disclosed methods, as well as the methods themselves. These and other materials, steps, and/or elements are disclosed herein, and it is understood that when combinations, subsets, interactions, groups, etc. of these materials are disclosed, that while specific reference of each various individual and collective combination and permutation of these compounds may not be explicitly disclosed, each is specifically contemplated and described herein.

Depressive disorders are characterized by sadness severe enough or persistent enough to interfere with function and experiences major depressive episodes which alternate with episodes of mania (in the case of type I) or hypomania (in the case of type II). Mania is a syndrome characterized by a euphoric, expansive, or irritable mood lasting at least one week. In addition, at least three of the following symptoms persisted during the same time period: inflated self esteem and/or grandiosity, decreased need for sleep, increased volume or rate of speech, flight of ideas and/or racing thoughts, distractibility, increased goal-directed activity and/or psychomotor agitation, excessive involvement in pleasurable activities that have a high potential for painful consequences. Mania and hypomania have similar signs and symptoms but are distinguished by the degree to which they result in impaired social and occupational functioning.

Bipolar affective disorder is characterized by two or more episodes in which the patient's mood and activity levels are significantly disturbed, this disturbance consisting on some occasions of an elevation of mood and increased energy and activity (hypomania or mania) and on others of a lowering of mood and decreased energy and activity (depression). Repeated episodes of hypomania or mania only are classified as bipolar. This includes manic depressive illness, psychosis, and reaction. This excludes bipolar disorder, single manic episode and cyclothymia.

In Bipolar affective disorder, current episode mild or moderate depression, the patient is currently depressed, as in a depressive episode of either mild or moderate severity, and has had at least one authenticated hypomanic, manic, or mixed affective episode in the past.

In Bipolar affective disorder, current episode severe depression without psychotic symptoms, the patient is currently depressed, as in severe depressive episode without psychotic symptoms, and has had at least one authenticated hypomanic, manic, or mixed affective episode in the past.

Treatment-resistant depression is exemplified by a case in which a human patient with either major depressive disorder or bipolar disorder continues to meet criteria for a major depressive episode in spite of treatment with conventional antidepressant drugs at adequate doses and treatment durations (at least 4 to 8 weeks).

Anxiety is a distressing, unpleasant emotional state of nervousness and uneasiness. Anxiety is less tied to the exact timing of a threat; it can be anticipatory before a threat, persist after a threat has passed, or occur without an identifiable threat. Anxiety is often accompanied by physical changes and behaviors similar to those caused by fear, which is an emotional, physical, and behavioral response to an immediately recognizable external threat.

Panic disorder is an episodic paroxysmal anxiety syndrome characterized by recurrent attacks of severe anxiety (panic) which are not restricted to any particular situation or set of circumstances and are therefore unpredictable. The symptoms include sudden onset of palpitations, chest pain, dyspnea, dizziness, and feelings of unreality (depersonalization or derealization). There is often also a secondary fear of dying, losing control, or going insane. Panic disorder may be seen with or without agoraphobia, which is characterized by a cluster of phobias embracing fears of leaving home, entering shops, crowds and public places, or traveling alone in trains, buses or planes. Avoidance of the phobic situation is prominent, to an extent that agoraphobics alter their lifestyles to avoid their relevant phobic situations.

Social phobia (also called Social Anxiety Disorder) is characterized by a marked and persistent fear of one or more social or performance settings in which the patient is exposed to unfamiliar people or to possible scrutiny by other people. The patient fears that in such situation they will act in a way (or show anxiety symptoms) that will be humiliating or embarrassing. Exposure to the feared social situation almost invariably provokes anxiety, and this response may progress to panic attacks. The feared social or performance situations are avoided, or else are endured with intense anxiety and distress.

Stress is any uncomfortable emotional experience uncomfortable emotional experience in response to any demand, accompanied by predictable biochemical, physiological and behavioral changes. Stress is often described as a feeling of being overwhelmed, worried or run-down, which can lead to both physical and psychological health issues. Excessive chronic stress, which is constant and persists over an extended period of time, can have health consequences and adversely affect the immune, cardiovascular, neuroendocrine and central nervous systems. Chronic stress can occur in response to everyday stressors that are ignored or poorly managed, as well as to exposure to traumatic events, such as acute stress disorder (ASD) or post-traumatic stress disorder (PTSD). Furthermore, chronic stress can cause or exacerbate health problems such as anxiety and depression, particularly when the stress is not properly managed.

PTSD arises as a delayed or protracted response to a stressful event or situation (of either brief or long duration) of an exceptionally threatening or catastrophic nature which is likely to cause pervasive distress in almost anyone. Predisposing factors, such as personality traits or previous history of mood or anxiety disorders, may lower the threshold for the development of the syndrome or aggravate its course, but they are neither necessary nor sufficient to explain its occurrence. Typical features include episodes of repeated reliving of the trauma in intrusive memories ("flashbacks"), dreams or nightmares occurring against the persisting background of a sense of "numbness" and emotional blunting, detachment from other people, unresponsiveness to surroundings, anhedonia, and avoidance of activities and situations reminiscent of the trauma. There often is a state of autonomic hyperarousal with hypervigilance, an enhanced startle reaction, and insomnia. Anxiety and depression commonly are associated with these symptoms and signs. The onset follows the trauma with a latency period that may range from a few weeks to months.

Generalized anxiety disorder is a chronic anxiety syndrome characterized by excessive worry or anxiety over a period lasting at least 6 months. These symptoms are associated with at least 3 of the following 6 symptoms: 1) restlessness or feeling on edge, 2) feeling easily fatigued, 3) impaired concentration, 4) irritability, 5) muscle tension, and 6) sleep disturbance. These anxiety symptoms are generalized and persistent but not restricted to, or even strongly predominating in, any particular environmental circumstances. The anxiety syndrome is sufficiently severe to cause clinically significant distress or to impair social or occupational functioning.

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects.

"Administering" and "administration" refer to methods of providing a pharmaceutical preparation to a subject. Such methods are known to those skilled in the art and include, but are not limited to, administering the compositions orally, parenterally (e.g., intravenously and subcutaneously), by intramuscular injection, by intraperitoneal injection, intrathecally, transdermally, extracorporeally, topically or the like.

A composition can also be administered by topical intranasal administration (intranasally) or administration by inhalant. As used herein, "topical intranasal administration" means delivery of the compositions into the nose and nasal passages through one or both of the nares and can comprise delivery by a spraying mechanism (device) or droplet mechanism (device), or through aerosolization of the composition. Administration of the compositions by inhalant can be through the nose or mouth via delivery by a spraying or droplet mechanism. As used herein, "an inhaler" can be a spraying device or a droplet device for delivering a composition comprising the MC5R peptide ligand, in a pharmaceutically acceptable carrier, to the nasal passages and the upper and/or lower respiratory tracts of a subject. Delivery can also be directly to any area of the respiratory system (e.g., lungs) via intratracheal intubation. The exact amount of the compositions required will vary from subject to subject, depending on the species, age, weight and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, for example, U.S. Pat. No. 3,610,795, which is incorporated by reference herein.

A "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of the composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

As described above, the compositions can be administered to a subject in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semi-permeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. A preferred mode of administration of the composition is orally. Other modes of administration may be topically (including ophthahnically, vaginally, rectally, intranasally), by inhalation, or parenterally, for example by intravenous drip, subcutaneous, intraperitoneal or intramuscular injection. The disclosed compounds can be administered orally, intravenously, intraperitoneally, intramuscularly, subcutaneously, intracavity, or transdermally.

Pharmaceutical compositions for oral administration include, but are not limited to, powders or granules, suspensions or solutions in water or non-aqueous media, capsules, sachets, or tablets. Thickeners, flavorings, diluents, emulsifiers, dispersing aids or binders may be desirable. The composition of the MC5R peptide ligand can be administered to a subject orally in a dosage taken once daily or in divided doses. The medication can be administered for one day and then stopped if clinical improvement occurs rapidly. Furthermore, the medication can be administered as infrequently as once every 4 to 8 weeks. A person of skill, monitoring a subject's clinical response, can adjust the frequency of administration of the medication according to methods known in the art.

Preparations for parenteral administration include sterile aqueous or non-aqueous solutions, suspensions, and emulsions. Examples of non-aqueous solvents are propylene glycol, polyethylene glycol, vegetable oils such as olive oil, fish oils, and injectable organic-esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like may be necessary or desirable.

In one aspect, the MC5R peptide ligand can be administered in an intravenous dosage. This dosage can be administered to a subject once daily or in divided dosages throughout a day, as determined by methods known in the art. This dosage can be administered to a subject for one day and then stopped if the subject responds immediately, or the dosage can be administered on a daily basis until a clinical response is noted. It is contemplated that the dosage of the MC5R peptide ligand can be administered as infrequently as once every month or every two months, or at any interval in between, depending on a subject's clinical response to the medication. Thus, if a subject responds to one dosage of the MC5R peptide ligand, a person of skill may determine that further dosages of the medication can be withheld. Moreover, if a subject does not respond to the initial dosage and administration of the MC5R peptide ligand, a person of skill can administer the medication daily for several days until such response occurs. A person of skill can monitor a subject's clinical response to the administration of the MC5R peptide ligand, and administer additional dosages if the subject's mood disorder symptoms reappear after a period of remission. It is contemplated that the MC5R peptide ligand can be administered to a subject with, for example, major mood disorder on a twice daily basis, once daily basis, on an alternating daily basis, on a weekly basis, on a monthly basis, or at any interval in between.

In another aspect, the MC5R peptide ligand can be administered to a subject transdermally, by using an adherent patch, by using iontophoresis, or by using any other method known to a person of skill. The dosage of the MC5R peptide ligand, administered transdermally can be given daily or infrequently as once every week or every 2-8 weeks. A person of skill, monitoring a subject's clinical response and improvement, can determine the frequency of administration of the medication by methods known in the art.

In another aspect, the MC5R peptide ligand can be administered to a subject intranasally in a dosage taken once daily or in divided doses. The medication can be administered for one day and then stopped if clinical improvement occurs rapidly. Further, the medication can be administered as infrequently as once every 4 to 8 weeks. A person of skill, monitoring a subject's clinical response to the administration of the medication, can adjust the frequency of administration according to methods known in the art.

In another aspect, the MC5R peptide ligand can be administered to a subject intramuscularly in a dosage taken once daily or in divided doses. The medication can be administered for one day and then stopped if clinical improvement occurs rapidly. Furthermore, the medication can be administered as infrequently as once every 4 to 8 weeks. A person of skill, monitoring a subject's clinical response, can adjust the frequency of administration of the medication according to methods known in the art.

EXAMPLES

The following examples are included to demonstrate certain embodiments of the invention. It should be appreciated by those of skill in the art that the techniques disclosed in the examples which follow represent techniques discovered by the inventors to function well in the practice of the invention, and thus are considered to constitute certain aspects for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Transdermal Administration of the MC5R Peptide Ligand

The following example describes treatment strategies for depression involving transdermal administration of the MC5R peptide ligand.

Six weeks after a 30 year old female gives birth to her first child, a follow up appointment with her obstetrician reveals that she is suffering from post-partum depression. The patient is experiencing excessive crying, difficulty bonding with her baby, overwhelming fatigue, intense anger and sadness, and severe anxiety and panic attacks. She further reports that in some instances, she has thoughts of suicide and harm coming to her baby. The female takes the Edinburgh Post Natal Depression Scale (EPDS) test, in which she scores a 25. A score of 10 or greater indicates possible perinatal mood or anxiety disorder. Her obstetrician refers her to a psychiatrist, who officially diagnoses her with postpartum depression. The psychiatrist recommends a trial of the MC5R peptide ligand administered using a transdermal patch. The patient is given a patch comprising the MC5R peptide ligand dose of 5 mg for transdermal delivery over a period 24 hours. A patch is to be administered every day for two weeks, followed by a visit with her psychiatrist. During her follow up visit with her psychiatrist, the patient retakes the EPDS test and scores a 12. She reports that her symptoms have drastically lessened in the past two weeks. Her psychiatrist prescribes another treatment of a transdermal patch comprising the MC5R peptide ligand dose of 1 mg for transdermal delivery over a period 24 hours. The patch is to be administered every other day for two weeks, followed by a visit with her psychiatrist. The patient continues to improve and is no longer suffering from post-partum depression two months later. No side effects are reported.

EXAMPLE 2

Oral Administration of the MC5R Peptide Ligand

The following example describes treatment strategies for depression and anxiety involving oral administration of the MC5R peptide ligand.

A 40-year-old male, who recently came back home from his tour of duty, reports to his psychiatrist that he is feeling depressed and having panic attacks. He further reveals that he is having flashbacks and nightmares, as well as feelings of detachment and outburst of extreme anger, which is causing him to have problems with his wife and child. His psychiatrist diagnoses him with PTSD and prescribes an oral medication of a formulation comprising the MC5R peptide ligand in a dose of 1 mg per tablet. The patient is to take the tablet twice a day for one week. The patient is highly responsive and experiences a reduction in his symptoms during the initial treatment period. After the initial treatment, the patient is prescribed to take a tablet of 0.05 mg of the MC5R peptide ligand once a day for another two weeks. The patient continues to improve and is functioning normally after one month. No side effects are reported.

EXAMPLE 3

Repeated Administration of a Fixed Dose IV

The following example describes a treatment strategy for depression involving the repeated administration of the MC5R peptide ligand.

A 52 year old female has a strong family history of depression and has had disabling depression since her teens. She has been tried on numerous oral medications without benefit. At times she is agitated and has panic attacks, which fluctuates with lethargy and insomnia. She is referred to a neurologist, who rules out any secondary causes for her symptoms. Her brain MRI scan and routine lab testing is within normal limits. Her psychiatrist recommends a trial of the MC5R peptide ligand administered intravenously. A fixed IV of the MC5R peptide ligand dose (0.01 mg/kg infusion over 30 minutes) is repeated administered every two days over a two week period in the hospital. A follow up visit with her psychiatrist reveals improving depression symptoms with less agitation, improved energy levels and sleep patterns. A second treatment of the fixed IV of the MC5R peptide ligand is given two months later. The patient continues to improve and is functioning normally at 6 months. No side effects are reported.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

```
                        SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: synthetic melanocortin 5 receptor (MC5R)
      peptide ligand
<220> FEATURE:
<221> NAME/KEY: MISC_FEATURE
<222> LOCATION: (1)..(1)
<223> OTHER INFORMATION: Xaa is cyclohexylalanine (Cha) or Pro.
<220> FEATURE:
<221> NAME/KEY: MISC_FEATURE
<222> LOCATION: (1)..(5)
<223> OTHER INFORMATION: Cyclization via 3-nitrobenzoic acid linking S
      in the side chain of Cys to the amine at the N-terminal of Xaa.
<220> FEATURE:
<221> NAME/KEY: MISC_FEATURE
<222> LOCATION: (2)..(2)
<223> OTHER INFORMATION: D-Phe

<400> SEQUENCE: 1

Xaa Phe Arg Trp Cys
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic MC5R peptide ligand
<220> FEATURE:
<221> NAME/KEY: MISC_FEATURE
<222> LOCATION: (1)..(1)
<223> OTHER INFORMATION: Xaa is Cha.
<220> FEATURE:
<221> NAME/KEY: MISC_FEATURE
<222> LOCATION: (1)..(5)
<223> OTHER INFORMATION: Cyclization via 3-nitrobenzoic acid linking S
      in the side chain of Cys to the amine at the N-terminal of Cha.
<220> FEATURE:
<221> NAME/KEY: MISC_FEATURE
<222> LOCATION: (2)..(2)
<223> OTHER INFORMATION: D-Phe

<400> SEQUENCE: 2
```

```
Xaa Phe Arg Trp Cys
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic MC5R peptide ligand
<220> FEATURE:
<221> NAME/KEY: MISC_FEATURE
<222> LOCATION: (1)..(1)
<223> OTHER INFORMATION: Xaa is Pro.
<220> FEATURE:
<221> NAME/KEY: MISC_FEATURE
<222> LOCATION: (1)..(5)
<223> OTHER INFORMATION: Cyclization via 3-nitrobenzoic acid linking S
      in the side chain of Cys to the amine at the N-terminal of Pro
<220> FEATURE:
<221> NAME/KEY: MISC_FEATURE
<222> LOCATION: (2)..(2)
<223> OTHER INFORMATION: D-Phe

<400> SEQUENCE: 3

Pro Phe Arg Trp Cys
1               5
```

What is claimed is:

1. A method of treating a depressive disorder or an anxiety disorder in a subject in need of such treatment, said method comprising administering to the subject a therapeutically effective amount of a composition comprising a melanocortin 5 receptor (MC5R) peptide ligand according to the following:

(SEQ ID NO: 1)

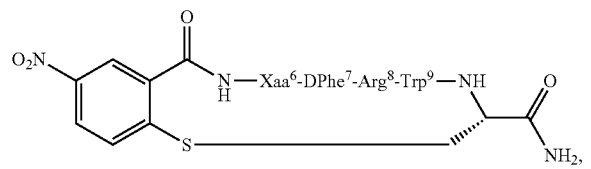

wherein Xaa is cyclohexylalanine (Cha) or Pro, wherein the MC5R peptide ligand is an MC5R antagonist that blocks MC5R.

2. The method of claim 1, wherein the subject is a mammal.

3. The method of claim 1, wherein the composition is administered in a dosage of about 0.001 mg/kg to 100 mg/kg of body weight.

4. The method of claim 1, wherein the composition is administered once daily or twice daily.

5. The method of claim 1, wherein the composition is administered at least once daily, at least once every other day, or at least once weekly.

6. The method of claim 1, wherein the composition is administered intravenously, transdermally, or orally.

7. The method of claim 1, wherein administration of the composition treats the disorder in the subject such that clinical improvement is observed in about 1 to 14 days.

8. The method of claim 1, wherein the MC5R peptide ligand is according to the following:

(SEQ ID NO: 2)

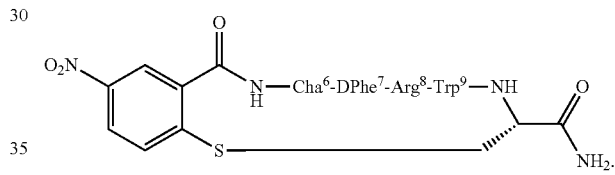

9. The method of claim 1, wherein the MC5R peptide ligand is according to the following:

(SEQ ID NO: 3)

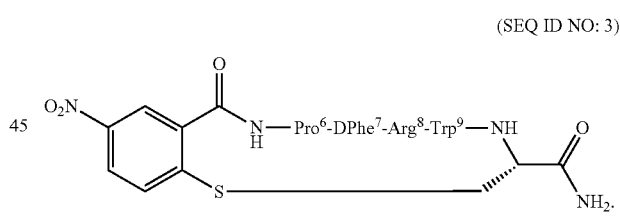

10. A method of treating a depressive disorder or an anxiety disorder, said method comprising determining that a subject has the depressive disorder or anxiety disorder, and administering to the subject a therapeutically effective amount of a composition comprising a melanocortin 5 receptor (MC5R) peptide ligand according to the following:

(SEQ ID NO: 1)

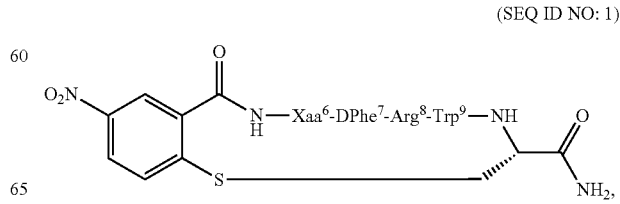

wherein Xaa is cyclohexylalanine (Cha) or Pro, wherein the MC5R peptide ligand is an MC5R antagonist that blocks MC5R.

11. The method of claim 10, wherein the subject is a mammal.

12. The method of claim 10, wherein the composition is administered in a dosage of about 0.001 mg/kg to 100 mg/kg of body weight.

13. The method of claim 10, wherein the composition is administered once daily or twice daily.

14. The method of claim 10, wherein the composition is administered at least once daily, at least once every other day, or at least once weekly.

15. The method of claim 10, wherein the composition is administered intravenously, transdermally, or orally.

16. The method of claim 10, wherein administration of the composition treats the disorder in the subject such that clinical improvement is observed in about 1 to 14 days.

17. The method of claim 10, wherein the MC5R peptide ligand is according to the following:

(SEQ ID NO: 2)

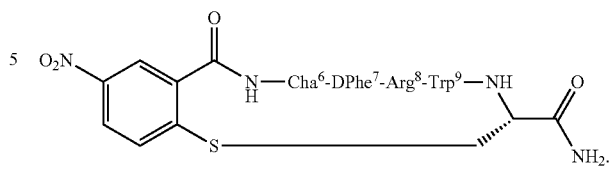

18. The method of claim 10, wherein the MC5R peptide ligand is according to the following:

(SEQ ID NO: 3)

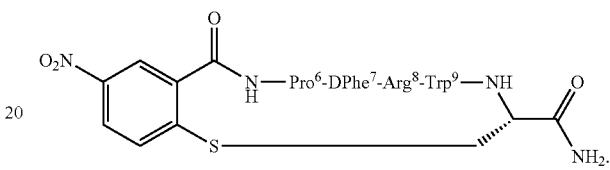

* * * * *